United States Patent
Kiyotomo et al.

(10) Patent No.: US 11,231,406 B2
(45) Date of Patent: Jan. 25, 2022

(54) GROUND INJECTION AGENT CONCENTRATION ESTIMATION METHOD

(71) Applicant: TAKENAKA CORPORATION, Osaka (JP)

(72) Inventors: Haruka Kiyotomo, Inzai (JP); Takaaki Shimizu, Inzai (JP); Tomohiro Nakashima, Inzai (JP); Yamato Shimizu, Inzai (JP); Nobuyasu Okuda, Inzai (JP); Yasuhide Furukawa, Inzai (JP); Yuji Yamazaki, Inzai (JP); Kazuhiro Mukai, Inzai (JP); Kaoru Inaba, Inzai (JP)

(73) Assignee: TAKENAKA CORPORATION, Osaka (JP)

( * ) Notice: Subject to any disclaimer, the term of this patent is extended or adjusted under 35 U.S.C. 154(b) by 0 days.

(21) Appl. No.: 16/348,755

(22) PCT Filed: Aug. 29, 2017

(86) PCT No.: PCT/JP2017/031018
§ 371 (c)(1),
(2) Date: May 9, 2019

(87) PCT Pub. No.: WO2018/087996
PCT Pub. Date: May 17, 2018

(65) Prior Publication Data
US 2019/0324008 A1    Oct. 24, 2019

(30) Foreign Application Priority Data
Nov. 14, 2016  (JP) .............................. JP2016-221687

(51) Int. Cl.
*G01N 33/24*  (2006.01)
*B09C 1/00*   (2006.01)
*G01N 21/64*  (2006.01)
*B09C 1/10*   (2006.01)

(52) U.S. Cl.
CPC ............. *G01N 33/24* (2013.01); *B09C 1/002* (2013.01); *B09C 1/10* (2013.01); *G01N 21/64* (2013.01); *B09C 2101/00* (2013.01)

(58) Field of Classification Search
CPC .... G01N 33/24; G01N 21/64; B09C 2101/00; B09C 1/002; B09C 1/02; B09C 1/08;
(Continued)

(56) References Cited

U.S. PATENT DOCUMENTS 4,783,314 A  *  11/1988  Hoots .................... G01F 1/704
                                                    210/696
5,120,661 A  *   6/1992  Baker .................... C23F 11/08
                                                    436/164
(Continued)

FOREIGN PATENT DOCUMENTS

CN       101424672 A       5/2009
CN       105973759 A1      9/2016
(Continued)

OTHER PUBLICATIONS

Barber, et al., "Fluorescent tracer technique for measuring the quantity of pesticide deposited to soil following spray applications," Crop Protection, vol. 22, No. 1, pp. 15-31, (2003).
(Continued)

*Primary Examiner* — Nam X Nguyen
*Assistant Examiner* — Julia L. Wun
(74) *Attorney, Agent, or Firm* — Alston & Bird LLP (57) ABSTRACT

A ground injection agent concentration estimation method including a injecting an injection liquid to which an injection agent and a marker exhibiting similar behavior in subsurface ground to that of the injection agent have been added, into the subsurface ground through a water injection well; measuring a concentration of the marker at a location spaced apart from the water injection well, and estimating a con-
(Continued)

centration of the injection agent in the groundwater from the concentration of the marker.

12 Claims, 8 Drawing Sheets

(58) Field of Classification Search
CPC .... B09C 1/01; C02F 1/008; C02F 1/68; C02F 1/685; C02F 1/686; C02F 2103/001; C02F 2103/06; C02F 2209/10; C02F 2209/105; C02F 2209/11; C02F 2209/003; C02F 2209/005; C02F 2209/006; C02F 2209/05
USPC ... 210/601, 747.7, 747.8, 170.07, 198.1, 94, 210/143, 745, 749
See application file for complete search history.

(56) References Cited

U.S. PATENT DOCUMENTS

| | | | | |
|---|---|---|---|---|
| 5,411,889 | A | * | 5/1995 | Hoots .................... G01N 33/18 436/6 |
| 2019/0120741 | A1 | | 4/2019 | Yang et al. |

FOREIGN PATENT DOCUMENTS

| | | |
|---|---|---|
| JP | 11057731 A | 3/1999 |
| JP | 2002119951 A | 4/2002 |
| JP | 2002250026 A | 9/2002 |
| JP | 2005-305282 A | 11/2005 |
| JP | 2010-000454 A | 1/2010 |
| JP | 2011173037 A | 9/2011 |
| JP | 2015-024401 A | 2/2015 |
| JP | 5971606 B1 | 8/2016 |
| JP | 2017-109188 A | 6/2017 |

OTHER PUBLICATIONS

EP 17868770.3 Extended European Search Report dated Jul. 20, 2020.
Duwig, et al."Quantifying fluorescent tracer distribution in allophanic soils to image solute transport," European Journal of Soil Science, vol. 59, No. 1, pp. 94-102, (2008).
CN 201780069363.0 Office Action dated Jul. 5, 2021, machine translation.

* cited by examiner

GROUND INJECTION AGENT CONCENTRATION ESTIMATION METHOD

CROSS REFERENCE TO RELATED APPLICATIONS

This application is a National Stage Application, filed under 35 U.S.C. § 371, of International Application No. PCT/JP2017/031018 filed Aug. 29, 2017, which claims priority to Japanese Application No. 2016-221687 filed Nov. 14, 2016; the contents of which are hereby incorporated by reference in their entirety.

BACKGROUND

Technical Field

The present disclosure relates to a ground injection agent concentration estimation method.

Description of Related Art

In a soil purification method disclosed in Japanese Patent Application Laid-Open (JP-A) No. 2005-305282 purification utilizing microorganisms is performed on contaminated soil. In such a soil purification method, a nitrate solution is injected into the contaminated soil as nutrient for the microorganisms, and the amount of nitrate solution injected is controlled by measuring the nitrate concentration in groundwater of the contaminated soil and determining when there is too much or too little of the nitrate solution.

BRIEF SUMMARY

JP-A No. 2005-305282 discloses directly measuring the concentration of the nitrate solution, which acts as nutrient for the microorganisms for purifying the contaminated soil, in the groundwater of the contaminated soil. However, it is sometimes difficult to measure a concentration of an injection agent for injection into the soil, such as a purification agent for injecting into the contaminated soil, an activator to promote a purification action of the purification agent, or the like.

In consideration of the above circumstances, an object of the present disclosure is to provide a ground injection agent concentration estimation method enabling a concentration of injection agent injected into ground to be estimated.

A ground injection agent concentration estimation method of a first aspect of the present disclosure includes injecting an injection liquid, to which an injection agent and a marker exhibiting similar behavior in ground to that of the injection agent have been added, into the ground through a water injection well, measuring a concentration of the marker in groundwater at a location spaced apart from the water injection well, and estimating a concentration of the injection agent in the groundwater from the concentration of the marker.

When an injection agent is injected into ground for the objective of contaminant purification, ground improvement, heat storage, water blocking, or the like, the concentration of the injection agent in groundwater needs to be appropriately managed in order to make the injection agent function effectively. However, sometimes sampled groundwater needs to be brought to a test laboratory and measured with bulky facilities in order to directly measure the concentration of the injection agent, and this takes effort to perform. Moreover, there is an issue in that sometimes measuring low concentrations of injection agent are difficult, or even though measurements are possible, it is difficult to discern whether or not the injection agent has arrived due to the injection agent dissolving and dispersing.

In the ground injection agent concentration estimation method of the first aspect of the present disclosure, the concentration of the marker in the groundwater is measured at a location spaced apart from the water injection well. The marker exhibits similar behavior in the ground to that of the injection agent, and this accordingly enables the concentration of the injection agent to be estimated from the concentration of the marker.

The concentration of the injection agent in the groundwater of the ground can accordingly be found. The injection agent can be caused to function effectively by appropriately managing the concentration of the injection agent in the groundwater in this manner.

A ground injection agent concentration estimation method of a second aspect of the present disclosure includes warming an injection liquid to which an injection agent is added, and injecting the injection liquid into ground through a water injection well, measuring an in-ground temperature at a location spaced apart from the water injection well, and estimating a concentration of the injection agent in the ground water from the in-ground temperature.

In the ground injection agent concentration estimation method of the second aspect of the present disclosure, the injection liquid for adding the injection agent is warmed, and the in-ground temperature is measured at the location spaced apart from the water injection well. The in-ground temperature is changed by the warmed injection liquid, and this enables the concentration of the injection agent to be estimated from changes to the in-ground temperature.

The concentration of the injection agent in the groundwater in the ground can accordingly be found. The injection agent can be caused to function effectively by appropriately managing the concentration of the injection agent in the groundwater in this manner.

In a ground injection agent concentration estimation method of a third aspect of the present disclosure, the injection agent is at least one of a purification agent to decompose a contaminant or an activator to activate biodecomposition by the purification agent.

The ground injection agent concentration estimation method of the third aspect of the present disclosure is able to purify the ground due to the purification agent or the activator being added to the injection liquid. The concentration of the purification agent or the activator in the groundwater of the ground needs to be appropriately managed in order to effectively decompose the contaminant in the ground. However, sometimes sampled groundwater needs to be brought to a test laboratory and measured with bulky facilities in order to directly measure the concentration of the purification agent or the activator, and this takes effort to perform.

However, in the ground injection agent concentration estimation method of the third aspect of the present disclosure, the concentration of the marker in the groundwater is measured at a location spaced apart from the water injection well. The marker exhibits similar behavior in the ground to that of the purification agent or the activator, and this accordingly enables the concentration of the purification agent or the activator to be estimated from the concentration of the marker.

The concentration of the purification agent or the activator in the groundwater of the ground can accordingly be found. The contaminant can accordingly be effectively decomposed by appropriately managing the concentration of the purification agent or the activator in the groundwater of the ground.

In a ground injection agent concentration estimation method of a fourth aspect of the present disclosure the marker is a fluorescent dye.

In the ground injection agent concentration estimation method of the fourth aspect of the present disclosure, the concentration of the purification agent or the activator is estimated from the concentration of the fluorescent dye in the groundwater at the location spaced apart from the water injection well. The concentration of the fluorescent dye can be measured quantitatively as light intensity using a fluorescence measurement instrument. This enables a certain degree of precision to be guaranteed.

In a ground injection agent concentration estimation method of a fifth aspect of the present disclosure, the purification agent and the activator are injected into the ground through the water injection well, and the marker includes one marker exhibiting similar behavior to the purification agent, and another different type of marker exhibiting similar behavior to the activator.

In the ground injection agent concentration estimation method of the fifth aspect of the present disclosure, the purification agent and the activator are injected into the ground. Different types of marker are then respectively employed for the purification agent and the activator. This accordingly enables the concentration of the purification agent and the activator to be estimated from these respective concentrations.

Thus even in cases in which the purification agent and the activator are mixed when injected into the ground, the respective concentrations thereof in the groundwater of the ground are able to be accurately estimated.

The ground injection agent concentration estimation method according to the present disclosure enables the estimation of a concentration of an injection agent injected into ground.

DETAILED DESCRIPTION

Explanation follows regarding exemplary embodiments of the present disclosure, with reference to the drawings. Note that explanation regarding common configuration elements represented by the same reference numerals in plural drawings is sometimes omitted.

First Exemplary Embodiment

Overall Configuration

Figure 1A:
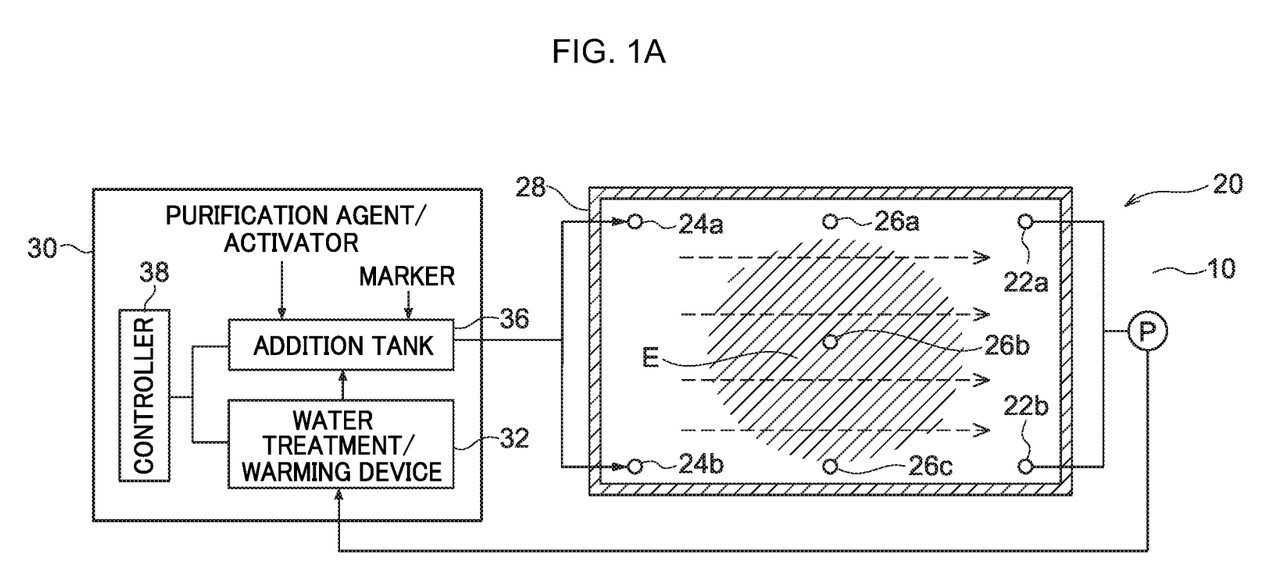
FIG. 1A is a plan view illustrating a schematic configuration of a ground injection agent concentration estimation system according to a first exemplary embodiment of the present disclosure.
Figure 1B:
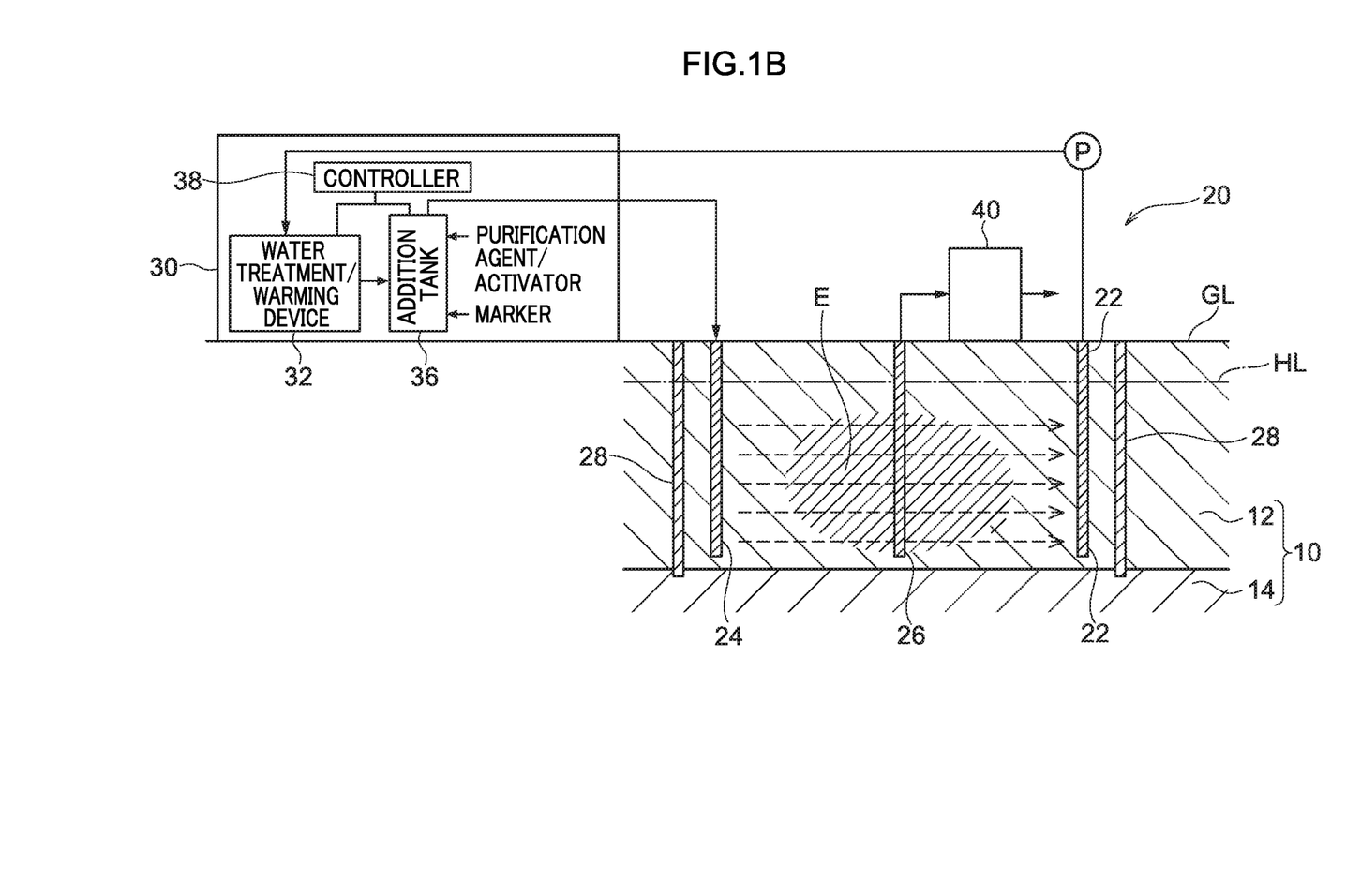
FIG. 1B is a vertical cross-section illustrating a schematic configuration of a ground injection agent concentration estimation system according to the first exemplary embodiment of the present disclosure.

A ground injection agent concentration estimation system of a first exemplary embodiment is applied to a contaminated ground purification system 20 illustrated in FIG. 1A and FIG. 1B for decomposing a contaminant contained in subsurface ground 10. The contaminated ground purification system 20 includes water pumping wells 22, water injection wells 24, observation wells 26, and a water-shielding wall 28 constructed in the subsurface ground 10, a purification unit 30 that is constructed above ground level GL and that circulates groundwater between the subsurface ground 10, the water pumping wells 22, and the water injection wells 24, and a measurement device 40 for analyzing groundwater sampled from the observation wells 26.

Contaminated Ground

The subsurface ground 10 is ground below the ground level GL, and includes an aquifer layer 12 through which groundwater flows, and an impermeable layer 14 through which groundwater does not flow. A portion of the subsurface ground 10 containing contaminant at a reference value or greater (for example a value set for each contaminant type) is referred to as contaminated ground E. The definition of "contaminant" includes organic substances such as tetrachloroethylene, trichloroethylene, cis-1,2-dichloroethylene, vinyl chloride monomers, benzene, and the like, inorganic compounds such as hexavalent chromium, cyan, and the like, and oils such as mineral oils like gasoline, diesel, and the like.

A groundwater level HL is indicated in FIG. 1B by a dotted-dashed line, and the direction of a flow of groundwater through the subsurface ground is indicated by dashed arrows. Note that the flow of groundwater is a flow generated by injecting an injection liquid containing a purification agent or the like, described later, into the subsurface ground 10 through the water injection wells 24, and by also pumping groundwater from the water pumping wells 22.

Water Pumping Wells

The water pumping wells 22 are water pumping means for pumping groundwater from the subsurface ground 10. Groundwater in the aquifer layer 12 may be drawn up by water pump P and fed to the purification unit 30. Although the water pump P is illustrated in FIG. 1A and FIG. 1B as being installed outside the water pumping wells 22 (water pumping wells 22a, 22b), this is merely for configuration explanation purposes, and the water pump P is actually installed inside the water pumping wells 22. However, the water pump P may be installed outside the water pumping wells 22. Moreover, the water pumping wells 22 are disposed between the contaminated ground E and the water-shielding wall 28, and the water pumping wells 22 are buried in the subsurface ground 10 such that a depth of lower ends of the water pumping wells 22 are at the depth of the contaminated ground E or deeper.

Although, for convenience, only the two water pumping wells 22a, 22b are illustrated in FIG. 1A, exemplary embodiments of the present disclosure are not limited thereto, and any appropriate number of the water pumping wells 22 may be disposed, according to the size of the site and so on.

Note that the water pumping wells 22 may be disposed in the contaminated ground E. Specific methods for pumping water using the water pumping wells 22, and the profile, size, and the like of the water pumping wells 22 are known, and so detailed explanation thereof is omitted.

Water Injection Wells

The water injection wells 24 (water injection wells 24a, 24b) are injection means used to inject injection liquid produced in the purification unit 30 into the subsurface ground 10. The injection liquid may be fed into the subsurface ground 10 using pumps and the like, not illustrated in the drawings. The water injection wells 24 are wells disposed between the contaminated ground E and the water-shielding wall 28 (on the opposite side to the water pumping wells 22 from the perspective of the contaminated ground E), and are buried in the subsurface ground 10 such that a depth of lower ends of the water injection wells 24 is at the depth of the contaminated ground E or deeper.

Although, for convenience, only the two water injection wells 24a, 24b are illustrated in FIG. 1A, exemplary embodiments of the present disclosure are not limited thereto, and any appropriate number of the water injection wells 24 may be disposed, according to the size of the site and so on.

Note that the water injection wells 24 may be disposed within the contaminated ground E. Specific methods for injecting the injection liquid using the water injection wells 24, and the profile, size, and the like of the water injection wells 24 are known, and so detailed explanation thereof is omitted.

Observation Wells

The observation wells 26 (observation wells 26a, 26b, 26c) are observation means for observing a subsurface state. Here, the "subsurface state" refers to a state in the subsurface ground 10 at positions where the observation wells 26 are buried. This includes, for example, a groundwater level, an in-ground temperature, a concentration in the groundwater of a later described purification agent, activator, and marker, and a concentration of a contaminant in the groundwater.

Various sensors, not illustrated in the drawings, are installed in the observation wells 26. The groundwater level, the in-ground temperature, the concentration and the like of the marker in the groundwater as mentioned above are measured by these sensors, and measured values thereof are transmitted as electrical signals to a controller 38 of the purification unit 30.

Note that sensors are also installed inside the water pumping wells 22 and the water injection wells 24. Namely, the respective water pumping wells 22 and water injection wells 24 also function as observation means. Signal lines connected to the respective sensors and to the controller 38 are omitted from illustration in FIG. 1A and FIG. 1B, in order to avoid increasing the complexity of the drawings.

Moreover, the non-illustrated water pump installed inside or outside the observation wells 26 is able to take a sample of groundwater at a predetermined depth in the observation wells 26, and to pump the sampled groundwater to the measurement device 40 installed above ground.

The observation wells 26 are buried at plural locations in the subsurface ground 10 enclosed by the water-shielding wall 28 and, for convenience, only the three observation wells 26a, 26b, 26c are illustrated in FIG. 1A. However, exemplary embodiments of the present disclosure are not limited thereto, and any appropriate number of the observation wells 26 may be disposed, according to the size of the site and so on.

Water-Shielding Wall

The water-shielding wall 28 is a water-shielding means made from steel poling plates (sheet pile) disposed in the subsurface ground 10 so as to enclose the periphery of the contaminated ground E and block the flow of groundwater between the inside and the outside of the water-shielding wall 28. Namely, the water-shielding wall 28 is disposed so as to the flow of groundwater in the subsurface ground 10 at the "outside" of the water-shielding wall 28 and the flow of groundwater in the subsurface ground 10 at the "inside" of the water-shielding wall 28 do not affect one another.

As illustrated in FIG. 1B, a lower end of the water-shielding wall 28 is embedded in the impermeable layer 14. The contaminated ground E is thus enclosed by the water-shielding wall 28 and the impermeable layer 14, suppressing the flow of contaminant out into the subsurface ground 10 on the outside of the water-shielding wall 28.

Purification Unit

The purification unit 30 is a device to purify the groundwater pumped from the water pumping wells by adding at least one of a purification agent and an activator, described later, to the groundwater, and returning the groundwater to the subsurface ground 10. The purification unit 30 is configured including a water treatment/warming device 32, an addition tank 36, and the controller 38.

Water Treatment/Warming Device

The water treatment/warming device 32 separates (and purges) volatile contaminants and oil from groundwater pumped from the water pumping wells. Moreover, the water treatment/warming device 32 warms the purified groundwater using a non-illustrated heater that is temperature-controlled by the controller 38, described later. Warming the groundwater using the water treatment/warming device 32 promotes reproduction of a decomposer microorganism that biodegrades contaminants in the subsurface ground 10, enabling the activity of the decomposer microorganism to be increased.

Addition Tank

The addition tank 36 produces injection liquid by adding to the groundwater at least one out of the purification agent and the activator, and a marker. Specifically, at least one out of the purification agent and activator, and the marker, are added to the groundwater inside the addition tank 36 from a feeder (not illustrated in the drawings) controlled by the controller 38, described later. This is then agitated to produce the injection liquid for injecting into the subsurface ground 10 through the water injection wells 24.

Note that purification agent and activator are examples of an injection agent of the present disclosure. The "purification agent" is a substance that decomposes the contaminant in the subsurface ground 10, and is, for example, a "decomposer microorganism" such as dehalococcoides, dehalosulphide, or the like for biodegrading the contaminant, or a "chemical decomposer" for chemically decomposing the contaminant. Specific examples of such a chemical decomposer include "reducing agents" such as an iron-based slurry or "oxidizing agents" such as hydrogen peroxide, a persulfate, Fenton's reagent, a permanganate, a percarbonate, or the like.

Note that in the first exemplary embodiment a decomposer microorganism (dehalococcoides) is employed as the purification agent. Moreover in the addition tank 36, an activator may also be added in addition to the purification agent, and detailed exemplary embodiments thereof are described below.

The "marker" is a substance exhibiting similar behavior in the subsurface ground 10 (including the contaminated ground E) to that of the purification agent or the activator, described later. The "marker" is also a substance whose concentration is easily measured in-situ (such as, for example, inside a building on or in the vicinity of the contaminated ground E) without employing bulky facilities, even when in a low concentration state. Examples thereof include a fluorescent dye, a halogen ion, a radioisotope, or the like. From among these, uranine, eosin, rhodamine B, rhodamine WT, pyranine, amino G acid, sodium naphthionate, sulforhodamine G, or the like may be employed as a fluorescent dye. A fluorescent dye (eosin) is employed in the first exemplary embodiment.

Reference here to "exhibiting similar behavior . . . to that of the purification agent or the activator" specifically means that the density, viscosity, adsorption/desorption characteristics, and the like of the marker with respect to the groundwater are about the same as those of the purification agent or the activator.

Moreover, "about the same as" includes cases in which there is a complete match, and cases in which a slight difference arises that is measurable in tests.

This means that the marker may be employed as a substance (tracer) to measure the concentration of the purification agent or the activator in the groundwater of the subsurface ground 10. The concentration of the purification agent or the activator in the groundwater of the subsurface ground 10 can be estimated by measuring the concentration of the marker.

Note that although in the present exemplary embodiment the injection liquid is produced by adding the marker to the groundwater in the addition tank 36, the concentration of the purification agent or the activator in the groundwater of the subsurface ground 10 can be estimated without employing the marker.

In such cases the temperature of the groundwater is measured. Namely, the injection liquid warmed in the water treatment/warming device 32 mixes with the groundwater of the subsurface ground 10 and raises the temperature thereof. The purification agent or the activator can accordingly be determined to have reached the location where the temperature is measured when the temperature of the groundwater becomes higher than before the start of injection of the injection liquid. Furthermore, the concentration of the purification agent or activator in the groundwater of the subsurface ground 10 can be estimated by measuring the change in this temperature.

Note that in temperature measurement the temperature of the groundwater does not necessarily always need to be measured in the observation well, and the temperature of the subsurface ground 10 may, for example, be measured by a thermocouple buried in the subsurface ground 10. Such a method to estimate the concentration of injection agent from the temperature of the subsurface ground 10 or the groundwater without employing the marker may also be applied in other exemplary embodiments.

Measurement Instrument

Figure 2:
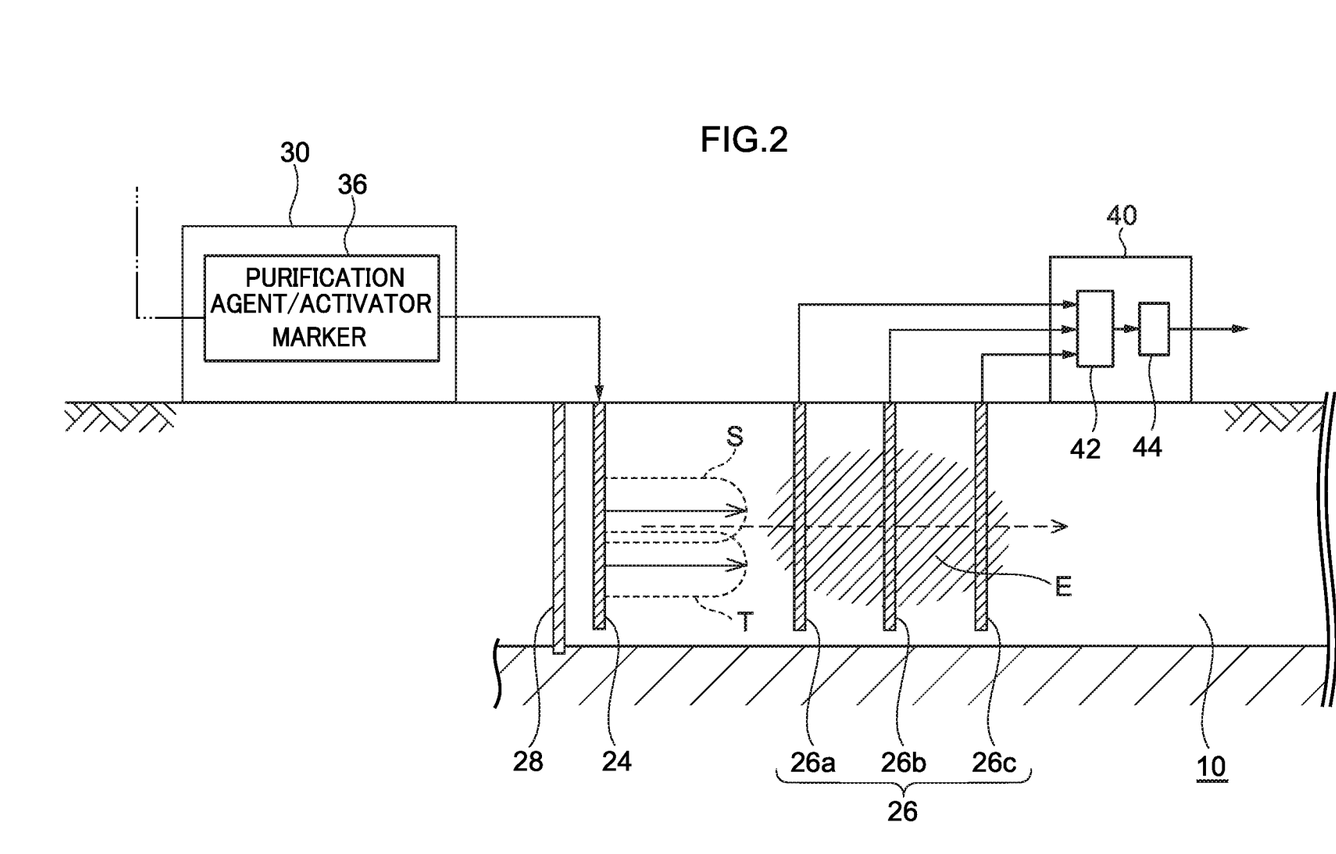
FIG. 2 is a vertical cross-section illustrating a relationship between an observation well and a measurement position in the ground injection agent concentration estimation system according to the first exemplary embodiment of the present disclosure.

FIG. 2 illustrates a vertical cross-section to explain a relationship between the observation wells 26 and the measurement device 40. The measurement device 40 is configured including a header 42 and a fluorescence measurement instrument 44.

The groundwater inside the observation wells 26a, 26b, 26c is pumped by pumping water from a predetermined depth using a non-illustrated water pump installed inside each of the wells, and is fed to the fluorescence measurement instrument 44 through the header 42 of the measurement device 40.

The header 42 is a consolidation pipe member to consolidate plural pipes into a single pipe. Opening or closing non-illustrated solenoid valves or valves therein enables selection of whichever groundwater is to be fed to the fluorescence measurement instrument 44 from out of the groundwater pumped from each of the observation wells 26a, 26b, 26c.

Figure 3:
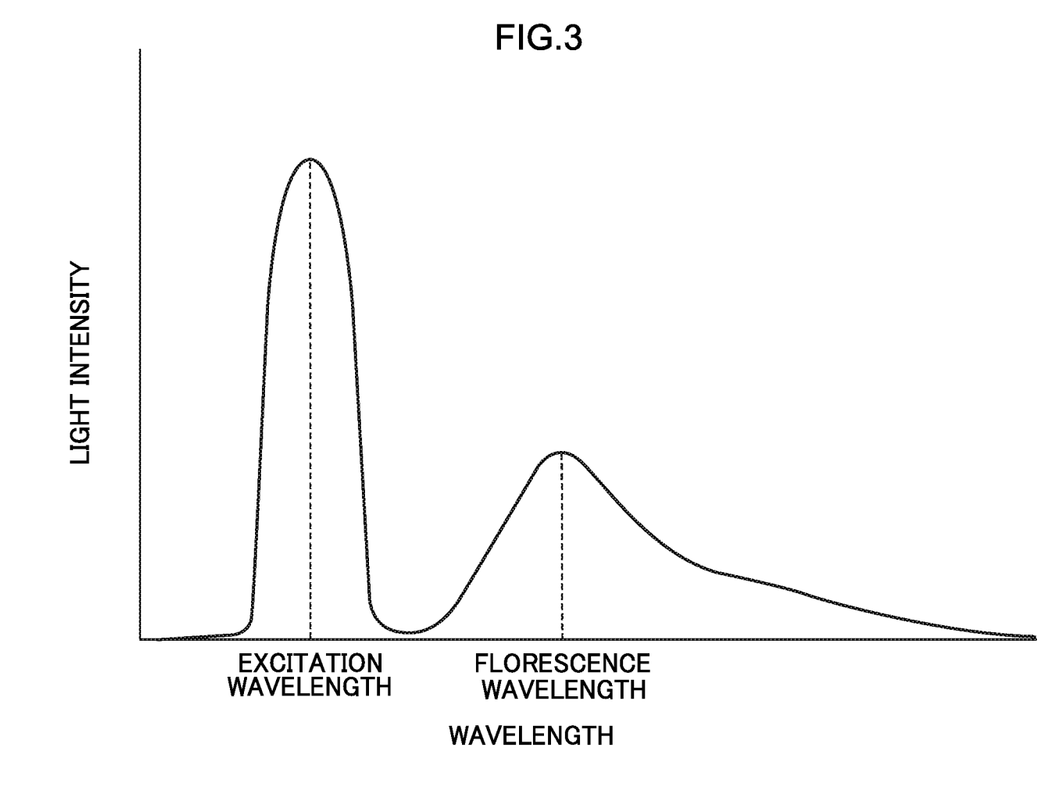
FIG. 3 is a graph illustrating relationships against wavelength for excitation light and fluorescence intensity in a measurement device in the ground injection agent concentration estimation system according to the first exemplary embodiment of the present disclosure.

The fluorescence measurement instrument 44 is able to measure the intensity of light emitted from the fluorescent dye serving as the marker contained in the groundwater that has been fed in from the header 42. More specifically, a light intensity C of fluorescence emitted by the fluorescent dye contained in the groundwater when excitation light has been illuminated from a light source device onto the groundwater can be measured. FIG. 3 illustrates a specific example of light intensities for the wavelengths of the excitation light and the wavelengths of the fluorescence.

The concentration of the fluorescent dye can be computed from the light intensity C. When the fluorescent dye concentration is expressed as a function of light intensity C, i.e. as $F(C)$ (mg/l), then an estimated concentration $X$ (mg/l) of the purification agent (decomposer microorganism) can be expressed in the following manner.

$$\text{(estimated purification agent concentration } X\text{)} = \alpha \times \text{(fluorescent dye concentration } F(C)\text{)} \quad \text{Equation (1)}$$

Wherein $\alpha$ is a coefficient.

The coefficient $\alpha$ is found from differences in adsorption/desorption characteristics measured by performing adsorption/desorption tests with the purification agent (decomposer microorganism) and the fluorescent dye. Note that although the adsorption/desorption characteristics of the marker with respect to the groundwater are, as stated above, about the same as those of the purification agent, there may be an amount of difference therebetween for which the coefficient $\alpha$ can be computed in this manner Controller The controller 38 receives, as electric signals, information regarding the groundwater level, the in-ground temperature, the concentration and the like of the fluorescent dye in the groundwater, and so on measured by the sensors respectively installed in the observation wells 26, the water injection wells 24, and the water pumping wells 22. The controller 38 controls driving of the water treatment/warming device 32, the addition tank 36, and the water pumps P according to the received information.

Measurement Method

In the ground injection agent concentration estimation system of the first exemplary embodiment, as illustrated in FIG. 2, first in the addition tank 36, the decomposer microorganism (dehalococcoides) serving as the purification agent, and the fluorescent dye (eosin) serving as the marker, are added to the injection liquid for injection into the subsurface ground 10 through the water injection wells 24. The concentration of the decomposer microorganism in the injection liquid and the fluorescent dye concentration in the injection liquid are made the same as each other in this case. Namely, the relationship between the respective concentrations in the injection liquid is expressed in the following manner.

$$\text{(decomposer microorganism concentration):(fluorescent dye concentration)} = 1:1 \quad \text{Equation (1-1)}$$

Next, the injection liquid, to which the decomposer microorganism (dehalococcoides) and the fluorescent dye (eosin) have been added, is injected from the addition tank 36 into the water injection wells 24. The injection liquid injected into the water injection wells 24 disperses from the water injection wells 24 into the subsurface ground 10 and the contaminated ground E at a target speed by generating a water gradient in the groundwater using the water pump P illustrated in FIG. 1A and FIG. 1B to pump groundwater from the water pumping wells 22.

When this is performed, due to the decomposer microorganism (dehalococcoides) and the fluorescent dye (eosin) having densities, viscosities, adsorption/desorption characteristics, and the like with respect to the groundwater that are about the same as those of the purification agent or the activator, the speeds of dispersing are about the same as each other, as respectively illustrated by S and T in FIG. 2.

However, the decomposer microorganism (dehalococcoides) and the fluorescent dye (eosin) have slightly different adsorption/desorption characteristics, and so differences arise in the concentration in the groundwater in the process of dispersing in the subsurface ground 10. The relationship between the respective concentrations in the groundwater is accordingly estimated in the following manner by employing the coefficient $\alpha$ that accords with the adsorption/desorption characteristics.

$$\text{(estimated decomposer microorganism concentration):(fluorescent dye concentration)} = \alpha:1 \quad \text{Equation (1-2)}$$

Next, the water pumps (not illustrated in the drawings) provided inside the observation wells 26a, 26b, 26c, which are provided at locations spaced apart from the water injection wells 24 as illustrated in FIG. 2, take samples of groundwater inside the observation wells 26a, 26b, 26c, and feed the groundwater to the fluorescence measurement instrument 44. The light intensity C of the fluorescent dye (eosin) is measured by the fluorescence measurement instrument, and the fluorescent dye (eosin) concentration F(C) (g/l) is computed therefrom.

Substituting the estimated decomposer microorganism concentration X (g/l) and the fluorescent dye (eosin) concentration F(C) (g/l) for the left side of Equation (1-2) yields the following expressions.

$$\text{(estimated decomposer microorganism concentration } X\text{):(fluorescent dye concentration } F(C)) = \alpha:1 \quad \text{Equation (1-3)}.$$

The Equation (1) above is obtained by modifying Equation (1-3), and the decomposer microorganism concentration is computed therefrom.

Note that although in the present exemplary embodiment the decomposer microorganism concentration in the injection liquid and the fluorescent dye concentration in the injection liquid are the same as each other, exemplary embodiments of the present disclosure are not limited thereto. For example, when the ratio between the decomposer microorganism concentration in the injection liquid and the fluorescent dye concentration in the injection liquid is (a:1), then the estimated decomposer microorganism concentration is computed by multiplying the right hand side of Equation (1) by a.

The value of "a" may be freely selected, however, since a contaminant decomposing effect is not expected from the fluorescent dye, the fluorescent dye may be contained at an amount needed to compute the decomposer microorganism concentration, and may be set at a=60, for example.

Operation and Advantageous Effects

When the injection liquid to which the decomposer microorganism has been added is diluted by the groundwater, the decomposer microorganism concentration in the groundwater becomes lower than a detection limit (of the order of $10^2$ copies/ml) measurable using an ordinary measurement method (quantitative PCR method such as quantitative real-time PCR). This makes it difficult to measure the decomposer microorganism concentration in the groundwater in a diluted state.

In contrast thereto, even when the fluorescent dye is diluted to a low concentration state in the groundwater, the light intensity can still be measured using the fluorescence measurement instrument. The fluorescent dye concentration can then be computed from the light intensity.

Moreover, the decomposer microorganism having the densities, viscosities, adsorption/desorption characteristics, and the like with respect to the groundwater that are about the same as those of the fluorescent dye. The decomposer microorganism concentration can accordingly be estimated as long as the fluorescent dye concentration in the groundwater is known.

The contaminant can accordingly be effectively decomposed by appropriately managing the decomposer microorganism concentration in the subsurface ground 10 and the groundwater of the contaminated ground E.

Second Exemplary Embodiment

Although in the first exemplary embodiment a fluorescent dye (eosin) is employed as the marker, a halogen ion is employed as the marker in a second exemplary embodiment. In such cases, the estimated purification agent (decomposer microorganism) concentration X (copies/ml) can be expressed in terms of a concentration G(D) (mg/l) of the marker (halogen ion) in the following manner Note that the concentration G(D) (mg/l) of the marker (halogen ion) is a function of the electrical conductivity D (S/m) measured using an electrical conductivity meter instead of the fluorescence measurement instrument 44.

$$(\text{estimated purification agent concentration } X) = \beta \times (\text{marker concentration } G(D)) \quad \text{Equation (2)}$$

Wherein $\beta$ is a coefficient.

The coefficient $\beta$ is, similarly to the coefficient $\alpha$ in Equation (1) of the first exemplary embodiment, found from differences in adsorption/desorption characteristics found by performing adsorption/desorption tests for the purification agent (decomposer microorganism) and the marker (halogen ion).

Note that the concentration $G(D)$ (mg/l) of the halogen ion serving as the marker may be computed as an ion concentration (mol/l) measured using an ion meter instead of an electrical conductivity meter.

Furthermore, as well as a halogen ion, a radioisotope may also be employed as the marker. In such cases, the marker concentration $G(D)$ (mg/l) in Equation (2) is computed from an amount of radiation (Bq) measured using a radiation measurement instrument.

Third Exemplary Embodiment

Although in the first and second exemplary embodiments it is a "purification agent" that is added to the injection liquid in the addition tank 36, in the third exemplary embodiment an "activator" is added instead of the "purification agent".

The "activator" is a substance that stimulates bio-decomposition by a decomposer microorganism, and a hydrogen releasing agent, an organic substance, a pH adjuster, micronutrients, trace elements, or the like may be employed as the activator.

Examples of organic substances that may be employed therefor include formic acid, acetic acid, propionic acid, butyric acid, lactic acid, or citric acid, sodium salts, potassium salts, or calcium salts thereof, glucose, fructose, galactose, lactose, maltose, trehalose, peptone, triptone, yeast extract, humic acid, plant oils, and the like.

Examples of pH adjusters that may be employed include sodium or potassium carbonates or bicarbonates such as sodium bicarbonate, sodium carbonate, and the like, ammonium hydroxide, ammonium carbonate, sodium tripolyphosphate, sodium diphosphate, sodium triphosphate, and the like.

Examples of micronutrients that may be employed include vitamin B12, vitamin B1, pantothenic acid, biotin, folate, and the like.

Examples of trace elements that may be employed include Co, Zn, Fe, Mg, Ni, Mo, B, and the like.

Due to these activators also having about the same densities, viscosities, adsorption/desorption characteristics, and the like with respect to groundwater as those of the marker, similarly to with the purification agent in the first exemplary embodiment, the concentration of the activator can be estimated using the marker.

In the present exemplary embodiment a yeast extract is employed as the activator, and a fluorescent dye (eosin) is employed as the marker. The estimated activator (yeast extract) concentration Y (mg/l) can be expressed in terms of the fluorescent dye concentration $F(C)$ (mg/l) in the following manner.

$$(\text{estimated activator concentration } Y) = \gamma \times (\text{fluorescent dye concentration } F(C)) \quad \text{Equation (3)}$$

Wherein $\gamma$ is a coefficient.

Fourth Exemplary Embodiment

Although a fluorescent dye is employed as the marker in the third exemplary embodiment, a halogen ion is employed as the marker in the fourth exemplary embodiment. In such cases, the estimated activator (yeast extract) concentration Y (mg/l) can be expressed in the following manner using a concentration $X(D)$ (mg/l) of the marker (halogen ion). Note that as well as halogen ions, a radioisotope may also be employed as the marker.

$$(\text{estimated activator concentration } Y) = \delta \times (\text{marker concentration } G(D)) \quad \text{Equation (4)}$$

Wherein $\delta$ is a coefficient.

Fifth Exemplary Embodiment

Although in the first to the fourth exemplary embodiments, one type of "purification agent" or "activator" is added as the "marker" to the injection liquid in the addition tank 36, both "purification agent" and "activator" are added as the "marker" in the fifth exemplary embodiment.

More specifically, a decomposer microorganism (dehalococcoides) and a chemical decomposer (hydrogen peroxide) are employed as the purification agent, and a yeast extract is employed as the activator. Moreover, a halogen ion is employed as the marker for the decomposer microorganism, a radioisotope is employed as the marker for the chemical decomposer, and a fluorescent dye is employed as the marker for the activator (yeast extract).

The concentration of the decomposer microorganism (dehalococcoides) and the chemical decomposer (hydrogen peroxide) serving as the purification agent are both estimated using Equation (2). However, the coefficient $\beta$ in Equation (2) is replaced as appropriate according to the respective adsorption/desorption characteristics of the decomposer microorganism (dehalococcoides), the chemical decomposer (hydrogen peroxide), the halogen ion, and the radioisotope. Moreover, the concentration of the activator (yeast extract) is estimated using Equation (3).

In the fifth exemplary embodiment, the respective concentrations of the decomposer microorganism, the chemical decomposer, and the activator can be estimated by measuring the concentration of the halogen ion, the amount of radiation of the radioisotope, and the light intensity of the fluorescent dye in the groundwater sampled from the observation wells 26.

Thus in cases in which the contaminated ground E is contaminated by a contaminant such as tetrachloroethylene and a contaminant such as hexavalent chromium, effective decomposition of the contaminant can be achieved by appropriately managing the respective concentrations of the "decomposer microorganism" and the "chemical decomposer" employed as the purification agents appropriate for the respective contaminant, and by appropriately managing the concentration of the "activator" employed to raise the activity of the decomposer microorganism.

Sixth Exemplary Embodiment

Although both purification agents and an activator are employed in the fifth exemplary embodiment, the exemplary embodiments of the present disclosure are no limitation thereto, and plural types of purification agent may be employed alone, or plural types of activator may be employed alone. Moreover, plural fluorescent dyes may be employed alone as the marker without employing a halogen ion or a radioisotope.

For example, in a sixth exemplary embodiment, a yeast extract and a hydrogen releasing agent (polylactate ester) are added as activators to the injection liquid, and different types of fluorescent dye (eosin and uranine) are employed as respective markers therefor.

This thereby enables the respective concentrations of the yeast extract and the hydrogen releasing agent (polylactate ester) to be estimated. Moreover, employing only the fluorescent dyes as markers eliminates the need to use an electrical conductivity meter or a radiation measurement instrument, enabling the concentration of the plural types of activator to be estimated using the fluorescence measurement instrument alone.

Combinations of the above exemplary embodiments may also be employed. For example, the fifth exemplary embodiment in which both "purification agents" and an "activator" and "markers" are added, may be combined with the sixth exemplary embodiment in which different types of fluorescent dye are employed as markers. In such cases, the injection liquid may, for example, have a decomposer microorganism added as a purification agent, a yeast extract added as an activator, a fluorescent dye (uranine) added as a marker for the decomposer microorganism, and a fluorescent dye (eosin) added as a marker for the yeast extract.

Namely, purification agents, activators, and markers may be combined freely, and various combinations may be employed. These combinations include one type of purification agent together with one type of marker, plural types of purification agent together with plural types of marker, one type of activator together with one type of marker, plural types of activator together with plural types of marker, one type of purification agent and one type of activator together with two types of marker, plural types of purification agent and plural types of activator together with plural types of marker, etc. However, a reducing agent (for example, an iron-based slurry) serving as a purification agent is preferably not employed in combination with an activator.

MODIFIED EXAMPLES

Explanation follows regarding various modified examples of the ground injection agent concentration estimation system according to the first to the fifth exemplary embodiments. For example, although in the first to the fifth exemplary embodiments, as illustrated in FIG. 1B, the contaminated ground E in the "single-layer" aquifer layer 12 formed above the impermeable layer 14 is purified, the exemplary embodiments of the present disclosure are not limited thereto. For example, as illustrated in FIG. 4B, the contaminated ground E1, E2 in "double-layer" aquifer layers 12A, 12B, formed by the aquifer layer 12 being interrupted in the vertical direction by an impermeable layer 16, may be purified. Alternatively a "multilayer" aquifer layer of three or more layers may also be purified.

When purifying the contaminated ground E1, E2 of the "double-layer" aquifer layers 12A, 12B, in addition to water pumping wells 22 (water pumping wells 22a, 22b), water injection wells 24 (water injection wells 24a, 24b), and observation wells 26 (observation wells 26a, 26b, 26c) installed in the lower aquifer layer 12B, water pumping wells 62 (water pumping wells 62a, 62b), water injection wells 64 (water injection wells 64a, 64b), and observation wells 66 (observation wells 66a, 66b) are also installed in the upper aquifer layer 12A.

Figure 4A:
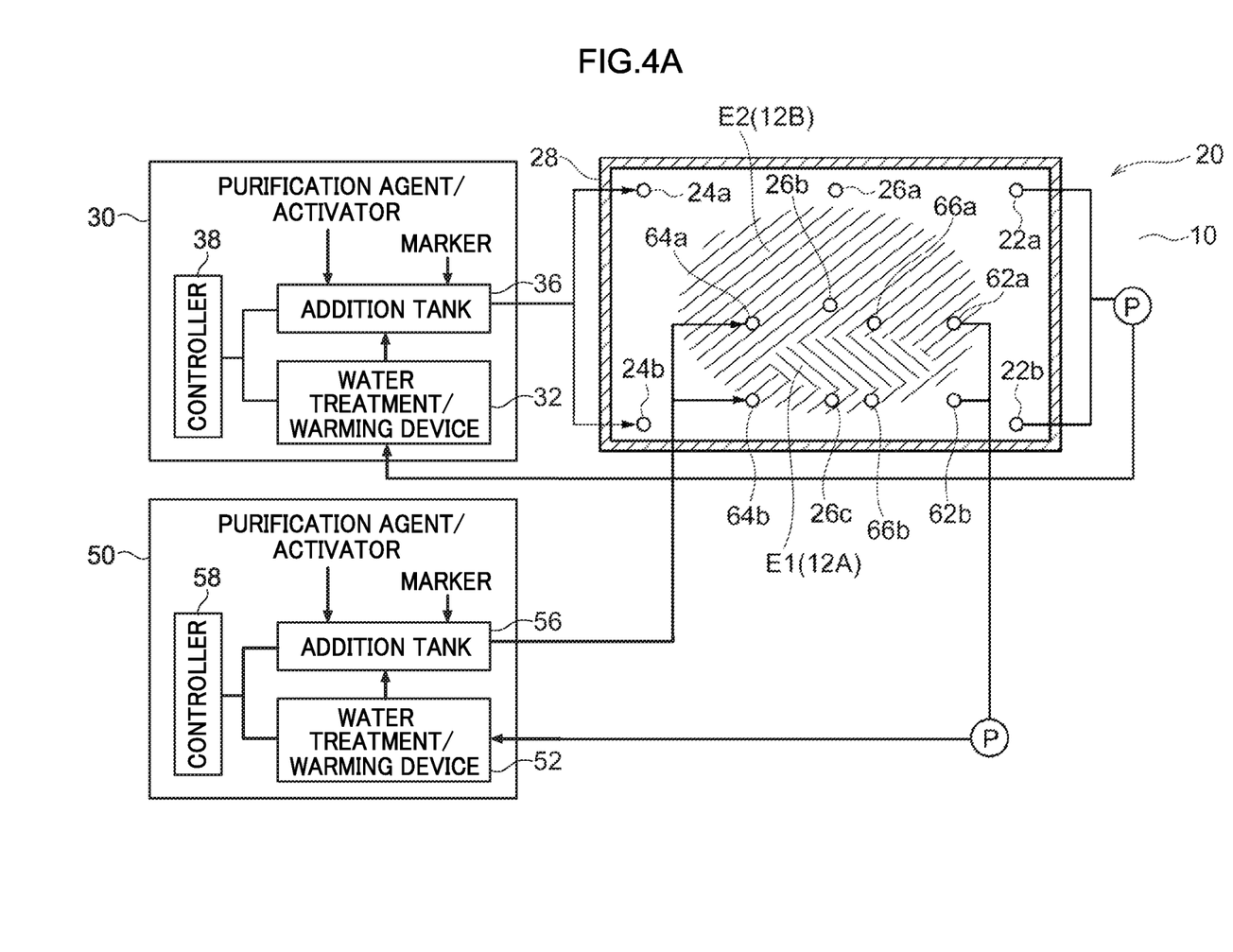
FIG. 4A is a plan view illustrating a modified example of purifying contaminated ground in double-layer aquifer layers formed by being interrupted in the vertical direction by an impermeable layer in a ground injection agent concentration estimation system according to the present exemplary embodiment of the present disclosure.
Figure 4B:
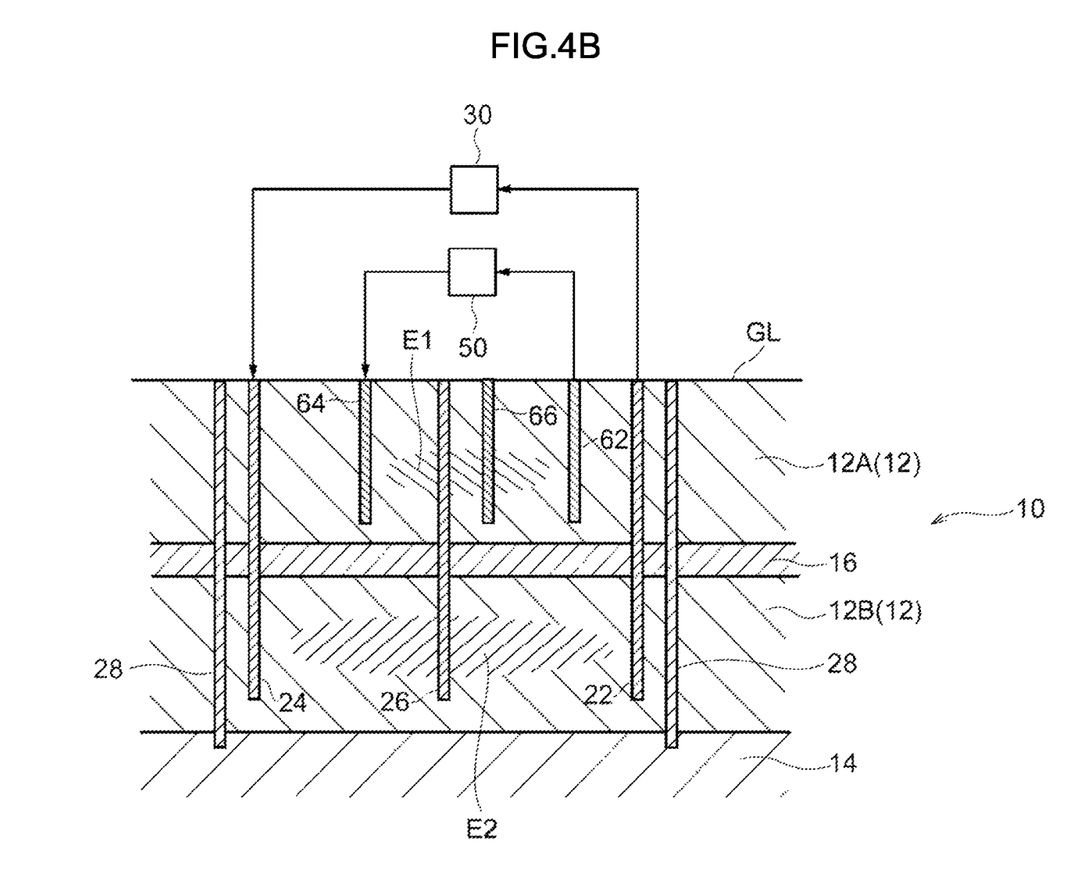
FIG. 4B is a vertical cross-section illustrating a modified example of purifying contaminated ground in double-layer aquifer layers formed by being interrupted in the vertical direction by an impermeable layer in a ground injection agent concentration estimation system according to the present exemplary embodiment of the present disclosure.

Then, as illustrated in FIG. 4A, in addition to a purification unit 30 for circulating groundwater between the aquifer layer 12B, the water pumping wells 22, and the water injection wells 24, a purification unit 50 is also provided for circulating groundwater between the aquifer layer 12A, the water pumping wells 62, and the water injection wells 64. This approach enables purification of the two aquifer layers 12A and 12B that are interrupted in the vertical direction by the impermeable layer 16. Similarly to the purification unit 30, the purification unit 50 also includes a water treatment/warming device 52, an addition tank 56, and a controller 58. Note that the controller 38 of the purification unit 30 and the controller 58 of the purification unit 50 may be consolidated into a single unit.

However, in cases in which fluorescent dyes are employed as markers for the purification agents purifying the aquifer layers 12A, 12B, there is a possibility of a fluorescent dye flowing from the aquifer layer 12A to the aquifer layer 12B through portions where the thickness of the impermeable layer 16 is thin or there are cracks therein, resulting in two fluorescent dyes mixing in the aquifer layer 12B. There is also the possibility of a fluorescent dye flowing from the aquifer layer 12B to the aquifer layer 12A such that two fluorescent dyes mix in the aquifer layer 12A.

Figure 5A:
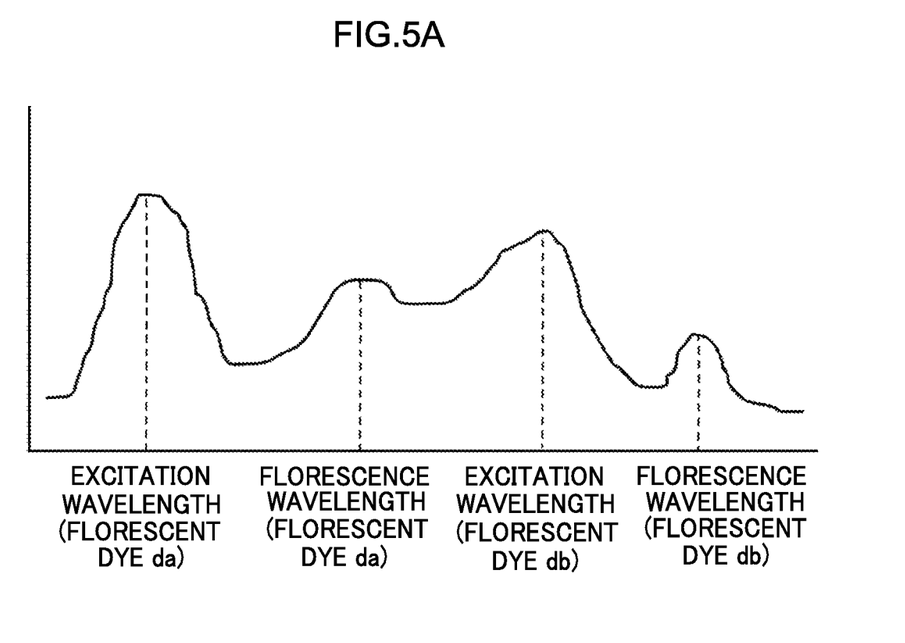
FIG. 5A is a graph illustrating relationships against wavelength for excitation light and fluorescence intensity for two types of fluorescent dye having respective excitation wavelength bands and fluorescence wavelength bands that are adjacent to each other in a measurement device in a ground injection agent concentration estimation system according to an exemplary embodiment of the present disclosure.

For example, as illustrated in FIG. 5A, when a fluorescent dye da and a fluorescent dye db have excitation wavelength bands and fluorescence wavelength bands that are mutually adjacent to each other, there is interference between the fluorescence wavelengths of the fluorescent dye da and the excitation wavelengths of the fluorescent dye db. This might accordingly make detection of the fluorescence wavelengths of the fluorescent dye da difficult.

Figure 5B:
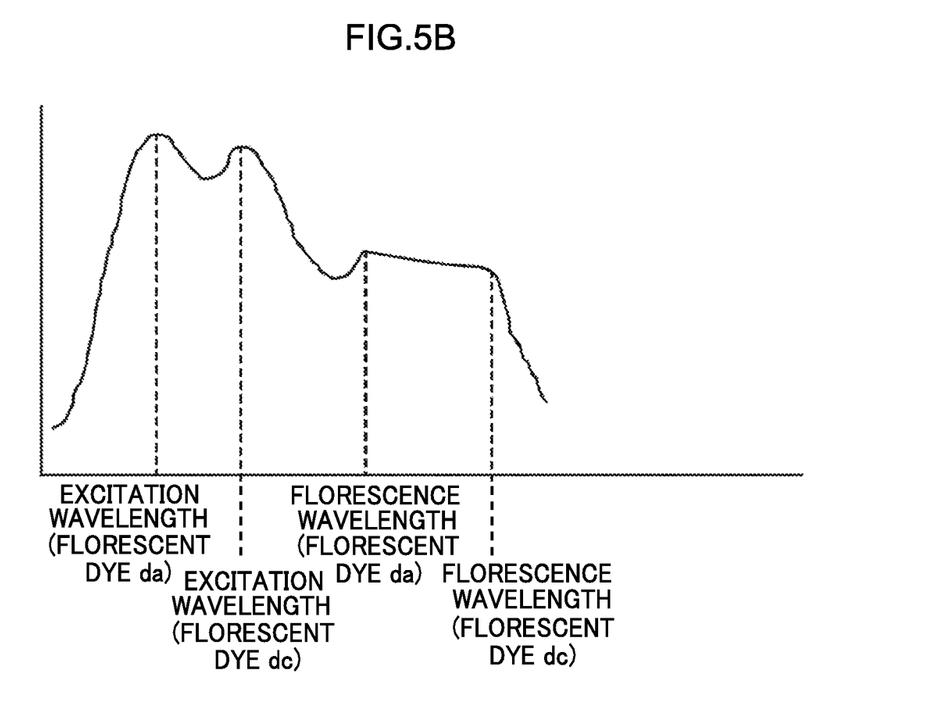
FIG. 5B is a graph illustrating relationships against wavelength for excitation light and fluorescence intensity for two types of fluorescent dye having respective excitation wavelength bands and fluorescence wavelength bands the overlap with each other in a measurement device in a ground injection agent concentration estimation system according to an exemplary embodiment of the present disclosure.

Moreover, as illustrated in FIG. 5B, when the fluorescent dye da and a fluorescent dye dc that have excitation wavelength bands and fluorescence wavelength bands that overlap with each other are mixed together, there is interference between the fluorescence wavelengths of the fluorescent dye da and the excitation wavelengths of the fluorescent dye dc. Moreover, there is also interference between the fluorescence wavelengths of the fluorescent dye da and the fluorescence wavelengths of the fluorescent dye dc. This might accordingly make detection of the fluorescence wavelengths of the fluorescent dye da and the fluorescence wavelengths of the fluorescent dye dc difficult.

Figure 5C:
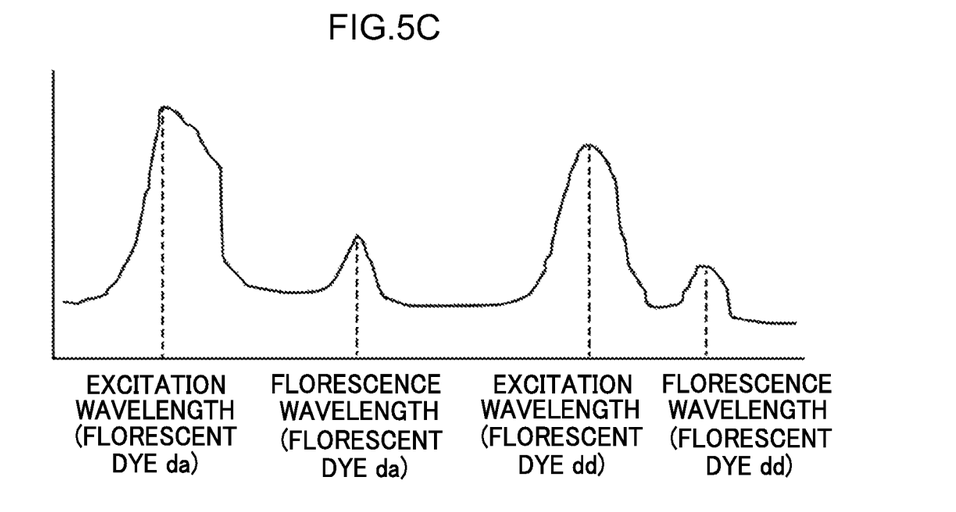
FIG. 5C is a graph illustrating relationships against wavelength for excitation light and fluorescence intensity for two types of fluorescent dye having respective excitation wavelength bands and fluorescence wavelength bands that are separated from each other in a measurement device in a ground injection agent concentration estimation system according to an exemplary embodiment of the present disclosure.

Thus in order to suppress interference between light such as that of the examples illustrated in FIG. 5A and FIG. 5B, the two fluorescent dyes employed in the aquifer layers 12A, 12B isolated from each other by the impermeable layer 16 are preferably selected such that there is sufficient separation between their respective excitation wavelength bands and fluorescence wavelength bands, such with the fluorescent dyes da, dd illustrated in FIG. 5C. Note that although examples illustrated in FIG. 5A and FIG. 5B show light interference that makes detection of the fluorescence wavelengths of the fluorescent dye da difficult, interference patterns are not limited thereto. For example, when there is interference between the excitation wavelengths of the fluorescent dye da and the fluorescence wavelengths or the excitation wavelength of a different fluorescent dye, then the fluorescence wavelengths of the fluorescent dye da is also sometimes affected so as to become difficult to detect.

Note that the same fluorescent dye may be employed as the marker for the purification agents to purify the aquifer layers 12A, 12B when the impermeable layer 16 illustrated in FIG. 4B is sufficiently thick, not cracked, etc. There is a low possibility of the fluorescent dye mixing in such cases even when the same fluorescent dye is employed therefor.

Moreover, although steel poling plates (sheet pile) is employed as the material of the water-shielding wall 28 illustrated in FIG. 1A and FIG. 1B in the first to the fifth exemplary embodiments, exemplary embodiments of the present disclosure are not limited thereto. For example, frozen earth, concrete, a cement-improved body, or the like may be employed therefor. Moreover, the water-shielding wall 28 does not necessarily need to be provided. In cases in which the water-shielding wall 28 is not provided, the water injection wells 24 are preferably disposed on an upstream side of a groundwater flow, and the water pumping wells 22 are preferably installed on the downstream side thereof. This enables injection liquid that has been injected into the subsurface ground 10 from the water injection wells 24 to be made to permeate smoothly into the subsurface ground 10.

Note that water quality improvement is performed in the first to the fifth exemplary embodiments by air being feed into the groundwater with the water treatment/warming device 32 illustrated in FIG. 1A and FIG. 1B. However, exemplary embodiments of the present disclosure are not limited thereto. For example, a method to perform water quality improvement by adding a purification agent to the groundwater to cause a reaction, or a method designed to separate contaminants from the groundwater by adsorption of the contaminants contained in the groundwater, may be employed as methods to perform water quality improvement.

Nutrient salts and oxygen may be mixed in, or fresh decomposer microorganism may be mixed in, as the purification agent in cases in which groundwater is purified by employing a decomposer microorganism to biodegrade a contaminant. Moreover, a flocculant may be mixed in to achieve smooth injection of the injection liquid using the water injection wells 24.

Although the groundwater purified in the water treatment/warming device 32 is warmed by a heater in the first to the fifth exemplary embodiments, exemplary embodiments of the present disclosure are not limited thereto. For example, the groundwater may be warmed by causing heat exchange to take place between a heating medium in an air conditioner unit (not illustrated in the drawings) and the groundwater purified in the water treatment/warming device 32. Furthermore, waste heat, steam or the like from a building on or in the vicinity of the contaminated ground E may be utilized for warming. Note that warming might not always be needed in cases such as those in which the decomposer microorganisms are already active at a predetermined activity level.

Note that although the ground injection agent concentration estimation system of each of the exemplary embodiments is applied to the contaminated ground purification system 20 for decomposing a contaminant contained in the subsurface ground 10, and the purification agent and the activator are employed as the injection agent, the exemplary embodiments of the present disclosure are not limited thereto.

For example, the ground injection agent concentration estimation system may be applied to a ground improvement system to counter liquefaction of the subsurface ground 10. In such cases, a supercooled aqueous solution, air bubble infused water, a solidification agent, or the like may be employed as the injection agent, and similarly to in the contaminated ground purification system 20, a fluorescent dye, halogen ion, radioisotope, or the like may be employed as the marker. Alternatively, the concentration of the injection agent may be estimated from temperature measurements of the groundwater instead of by using a marker.

Note that a supercooled aqueous solution is an aqueous solution such as erythritol, sodium acetate trihydrate, sodium acetate decahydrate, or the like for injection into the subsurface ground 10 in a super-cooled state. Crystals are then introduced or a shock is imparted thereto at the point in time when the concentration of the supercooled aqueous solution in the groundwater has reached a predetermined concentration, thereby inducing crystallization to occur. Ground improvement is thereby achieved by solidifying the subsurface ground 10.

Moreover, air bubble infused water is a liquid resulting from infusing water with fine bubbles (air bubbles having a diameter of 100 μm or less), microbubbles (air bubbles having a diameter of 1 to 100 μm), or ultrafine bubbles (air bubbles having a diameter of 1 μm or less). The air bubble infused water is then injected into the subsurface ground 10 so as to achieve a state in which the groundwater does not saturate the subsurface ground 10 and contains air bubbles at a predetermined concentration. The water pressure in pores between particles of the subsurface ground 10 is thereby suppressed from rising during an earthquake, enabling liquefaction to be made less liable to occur.

Moreover, a material that may be employed as the solidification agent may be: a liquid suspension type non-water-glass based solidification agent such as a clay/cement based (such as bentonite, cement, or the like), an ultrafine particle based (such as Highbrid Silica (registered trademark)), or a special slag based (such as SILACSOL (registered trademark)-UF or the like) non-waterglass based solidification agent; a liquid suspension type waterglass based solidification agent such as an alkali (RMG-S5 or the like) or a neutral/acidic (Creanfarm or the like) liquid suspension type waterglass based solidification agent; a waterglass based liquid type inorganic solidification agent such as an alkali (ALSILICA (registered trademark) or the like), a neutral/acidic (HARDLIZER (registered trademark) or the like), a special neutral/acidic (Ecoryon (registered trademark) or the like), a special silica (ECOSILICA (registered trademark) or the like) waterglass based liquid type inorganic solidification agent; or an alkali (RSG-3) waterglass based liquid organic solidification agent.

Furthermore, the ground injection agent concentration estimation system may be applied to a heat storage system utilizing heat in the ground of the subsurface ground 10. In such cases, a heat storage material such as a supercooled aqueous solution is employed as the injection agent, and similarly to in the contaminated ground purification system 20, a fluorescent dye, halogen ion, radioisotope, or the like is employed as the marker.

Note that erythritol, sodium acetate trihydrate, sodium acetate decahydrate, or the like have a relatively large heat capacity when employed as a supercooled aqueous solution, in comparison to water or concrete, and accordingly readily exhibit the functionality of a heat storage material.

Furthermore, the ground injection agent concentration estimation system may be applied as a water shielding system to reduce the groundwater level when excavating the subsurface ground 10. In such cases a supercooled aqueous solution or a solidification agent is employed as the injection agent, and similarly to in the contaminated ground purification system 20, a fluorescent dye, halogen ion, radioisotope, or the like is employed as the marker. Alternatively, the concentration of the injection agent may be estimated by measuring the temperature of the groundwater instead of by employing a marker.

The ground injection agent concentration estimation system according to the present disclosure may accordingly be implemented in various situations.

The disclosure of Japanese Patent Application No. 2016-221687, filed on Nov. 14, 2016, is incorporated in its entirety by reference herein. All cited documents, patent applications, and technical standards mentioned in the present specification are incorporated by reference in the present specification to the same extent as if each individual cited document, patent application, or technical standard was specifically and individually indicated to be incorporated by reference.

The invention claimed is:

1. A method of introducing a ground injection agent into groundwater, the method comprising:
injecting an injection liquid comprising one or more injection agent and one or more marker into the ground through a water injection well, wherein the one or more injection agent and one or more marker both being characterized by exhibiting a similar behavior in the ground;
measuring a concentration of the one or more marker in the groundwater, using a sensor, at a location spaced apart from the water injection well;
estimating a concentration of the one or more injection agent in the groundwater from the concentration of the one or more marker in the groundwater, and the ratio between a concentration of the one or more injection agent in the injection liquid and a concentration of the one or more marker in the injection liquid, and a coefficient based on a difference between a first absorption/desorption characteristic of the one or more marker and a second absorption/desorption characteristic of the one or more injection agent; and
adjusting the concentration of the one or more injection agent in the groundwater based on the estimated concentration of the one or more injection agent in the groundwater by controlling, through a controller, the injection of the injection liquid into the groundwater through the water injection well.

2. The method of claim 1, wherein the one or more injection agent is selected from the group consisting of a purification agent to decompose a contaminant and an activator to activate bio-decomposition by the purification agent.

3. The method of claim 2, wherein the one or more marker comprises one or more fluorescent dye.

4. The method of claim 3, wherein the one or more fluorescent dye is selected from the group consisting of uranine, eosin, rhodamine B, rhodamine WT, pyranine, amino G acid, sodium naphthionate, and sulforhodamine G.

5. The method of claim 2, wherein:
the purification agent and the activator are injected into the ground through the water injection well; and
the one or more marker comprises a first marker characterized by exhibiting similar behavior to the purification agent in the ground, and a second marker characterized by exhibiting similar behavior to the activator in the ground.

6. The method of claim 1, wherein the one or more injection agent and one or more marker both being characterized by exhibiting a similar behavior in the ground further comprises moving inside the ground at similar speeds.

7. A method of introducing a ground injection agent into groundwater, the method comprising:
injecting an injection liquid comprising one or more injection agent and one or more marker into the ground through a water injection well;
measuring a concentration of the one or more marker in the groundwater, using a sensor, at a location spaced apart from the water injection well;
estimating a concentration of the one or more injection agent in the groundwater from the concentration of the one or more marker in the groundwater, and the ratio between a concentration of the one or more injection agent in the injection liquid and a concentration of the one or more marker in the injection liquid, and a coefficient based on a difference between a first absorption/desorption characteristic of the one or more marker and a second absorption/desorption characteristic of the one or more injection agent; and
adjusting the concentration of the one or more injection agent in the groundwater based on the estimated concentration of the one or more injection agent in the groundwater by controlling, through a controller, the injection of the injection liquid into the groundwater through the water injection well,
wherein the one or more injection agent and one or more marker both comprise a property that are about the same, and
wherein the property comprises at least one of viscosity, adsorption characteristics, desorption characteristics.

8. The method of claim 7, wherein the one or more injection agent is selected from the group consisting of a purification agent to decompose a contaminant and an activator to activate bio-decomposition by the purification agent.

9. The method of claim 8, wherein the one or more marker comprises one or more fluorescent dye.

10. The method of claim 9, wherein the one or more fluorescent dye is selected from the group consisting of uranine, eosin, rhodamine B, rhodamine WT, pyranine, amino G acid, sodium naphthionate, and sulforhodamine G.

11. The method of claim 7, wherein the one or more injection agent and one or more marker both being characterized by exhibiting a similar behavior in the ground by moving inside the ground at similar speeds.

12. The method of claim 11, wherein:
the purification agent and the activator are injected into the ground through the water injection well; and
the one or more marker comprises a first marker characterized by exhibiting similar behavior to the purification agent in the ground, and a second marker characterized by exhibiting similar behavior to the activator in the ground.

* * * * *